(12) United States Patent
Hayakawa et al.

(10) Patent No.: US 6,599,239 B2
(45) Date of Patent: Jul. 29, 2003

(54) FLEXIBLE TUBE FOR ENDOSCOPE, MATERIAL USED FOR PRODUCING OUTER COVER OF THE FLEXIBLE TUBE, AND PRODUCTION METHOD OF THE FLEXIBLE TUBE

(75) Inventors: Shinji Hayakawa, Saitama (JP); Kensaku Ueki, Tokyo (JP)

(73) Assignee: Pentax Corporation, Tokyo (JP)

( * ) Notice: Subject to any disclaimer, the term of this patent is extended or adjusted under 35 U.S.C. 154(b) by 146 days.

(21) Appl. No.: 09/734,928

(22) Filed: Dec. 13, 2000

(65) Prior Publication Data
US 2001/0007917 A1 Jul. 12, 2001

(30) Foreign Application Priority Data

Dec. 13, 1999 (JP) .......................................... 11-353541

(51) Int. Cl.[7] .................................................. A61B 1/00
(52) U.S. Cl. ....................................... 600/139; 600/140
(58) Field of Search ................................ 600/139, 140, 600/121; 604/282; 425/125; 523/211

(56) References Cited

U.S. PATENT DOCUMENTS

| 4,368,280 A | * | 1/1983 | Yui et al. | .................... 523/211 |
| 4,573,896 A | * | 3/1986 | Bonzo | ......................... 425/125 |
| 5,394,864 A | | 3/1995 | Kobayashi et al. | |
| 5,448,988 A | | 9/1995 | Watanabe | |
| 5,685,825 A | * | 11/1997 | Takase et al. | ................. 600/140 |
| 5,688,221 A | * | 11/1997 | Yabe et al. | ................... 600/121 |
| 5,947,940 A | * | 9/1999 | Beisel | ............................ 604/282 |

FOREIGN PATENT DOCUMENTS

| JP | 362035315 A | * | 2/1987 | ........... G02B/23/24 |
| JP | 6-169887 | | 6/1994 | |
| JP | 6-67376 | | 8/1994 | |
| JP | 7-341 | | 1/1995 | |
| JP | 7-110270 | | 11/1995 | |

* cited by examiner

*Primary Examiner*—Teresa Walberg
*Assistant Examiner*—Leonid M Fastovsky
(74) *Attorney, Agent, or Firm*—Greenblum & Bernstein, P.L.C.

(57) ABSTRACT

A flexible tube for an endoscope includes a flexible elongated structural body and an outer cover provided over the elongated structural body. The outer cover is made of a material which contains polyurethane elastomer and polyester elastomer, in which compounding ratio of the polyurethane elastomer and the polyester elastomer in the material is 0.03–0.3 parts by weight of the polyester elastomer per 1 part by weight of the polyurethane elastomer. This flexible tube has excellent flexibility as well as various excellent properties such as chemical resistance, heat resistance and weather resistance.

20 Claims, 3 Drawing Sheets

FLEXIBLE TUBE FOR ENDOSCOPE, MATERIAL USED FOR PRODUCING OUTER COVER OF THE FLEXIBLE TUBE, AND PRODUCTION METHOD OF THE FLEXIBLE TUBE

BACKGROUND OF THE INVENTION

1. Field of the Invention

The present invention relates to a flexible tube for an endoscope, a material used for producing an outer cover of the flexible tube, and to a method of producing the flexible tube.

2. Description of the Prior Art

In an endoscopic examination, a flexible tube of an insertion section of an endoscope is to be inserted deep into the body cavity, for example, into the stomach, duodenum, small intestine or large intestine. For this reason, the flexible tube has to have sufficient flexibility (that is, the insertion section is required to have flexibility). This reduces the burden on patients. The flexible tube is roughly composed of a flexible elongated structural body (including an elongated coil) and an outer cover provided on the outer periphery of the structural body. The outer cover of the flexible tube serves to prevent body fluids and the like from entering the inside of the insertion section of the endoscope. In order to improve the ease of the inserting operation of the insertion section, the outer cover is also required to have sufficient flexibility. In the prior art, an elastic material such as polyurethane or the like has generally been used as a structural material for the outer cover of the flexible tube of the endoscope.

Now, because an endoscope is used repeatedly, it must be washed and sterilized after each use. However, such prior art materials have poor chemical resistance and heat resistance. Consequently, when such an endoscope is used repeatedly, the repeated sterilization of the endoscope using a peroxide disinfectant solution or high heat sterilizing treatment after each use will degrade the outer cover of the flexible tube. Further, as the outer cover of the flexible tube of the endoscope loses flexibility over time, it becomes difficult to smoothly insert the flexible tube into a body cavity. Furthermore, in the case where such degradation is severe, small cracks and the like will be created, and this can cause the outer cover of the flexible tube to partially peel off.

SUMMARY OF THE INVENTION

In view of the problems involved in the prior art described above, it is a main object of the present invention to provide an improved flexible tube for an endoscope having high chemical resistance and heat resistance as well as flexibility and a material used for producing the flexible tube.

Further, it is another object of the present invention to provide a method of producing such a flexible tube.

In order to achieve the above main objects, the present invention is directed to a flexible tube for an endoscope, comprising a flexible elongated structural body, and an outer cover provided over the elongated structural body, the outer cover being made of a material which contains polyurethane elastomer and polyester elastomer, in which compounding ratio of the polyurethane elastomer and the polyester elastomer in the material is 0.03–0.3 parts by weight of the polyester elastomer per 1 part by weight of the polyurethane elastomer.

Thus formed flexible tube has excellent flexibility as well as excellent properties such as chemical resistance and heat resistance.

In this invention, it is preferred that the weight average molecular weight of the polyester elastomer lies within the range of 10,000–50,000.

Use of the material containing the polyester elastomer having the weight average molecular weight makes it possible that the polyurethane elastomer and the polyester elastomer are uniformly mixed in the material.

In the present invention, it is also preferred that the polyurethane elastomer and the polyester elastomer are contained in the material in a uniformly mixed state.

Another aspect of the present invention is directed to a material used for producing an outer cover of a flexible tube for an endoscope. The material comprising polyurethane elastomer and polyester elastomer, in which compounding ratio of the polyurethane elastomer and the polyester elastomer in the material is 0.03–0.3 parts by weight of the polyester elastomer per 1 part by weight of the polyurethane elastomer.

In this case, it is preferred that the weight average molecular weight of the polyester elastomer lies within the range of 10,000–50,000. Further, it is also preferred that the polyurethane elastomer and the polyester elastomer are contained in the material in a uniformly mixed state.

Yet another aspect of the present invention is directed to a method of producing a flexible tube for an endoscope. The method comprises the steps of: preparing a material which contains polyurethane elastomer and polyester elastomer, in which compounding ratio of the polyurethane elastomer and the polyester elastomer in the material is 0.03–0.3 parts by weight of the polyester elastomer per 1 part by weight of the polyurethane elastomer; heating the prepared material to such an extent that the material is melted or softened; and molding the material onto a flexible elongated structural body to form an outer cover of the flexible tube in the form of an elongated tubular form to obtain the flexible tube.

This method is capable of providing a flexible tube for an endoscope which has excellent flexibility as well as excellent properties such as chemical resistance and heat resistance.

In this method, it is preferred that before the molding step, the temperature of the material is held at 140–230° C. This makes it possible to prevent the outer cover material from being hardened, deteriorated or degraded.

Further, it is also preferred that before the molding step, viscosity of the material lies within the range of $1.0 \times 10^2$–$1.0 \times 10^7$ ps. Use of such a material makes it possible to produce the outer cover of the flexible tube having good weather resistance.

Furthermore, it is also preferred that the weight average molecular weight of the polyester elastomer lies within the range of 10,000–50,000. This makes it possible that the polyurethane elastomer and the polyester elastomer are uniformly mixed in the material.

In this method, it is also preferred that in the material preparing step, the material is stirred so that the polyurethane elastomer and the polyester elastomer are uniformly mixed to each other. For this purpose, it is preferred that in the material preparing step, the material is poured into a cylinder provided with a mixing screw, and then the material is stirred with the mixing screw under heated condition.

In this case, preferably, the mixing screw in the cylinder is rotated at a rotation speed of 2.0–30 rpm. This makes it possible to mix the components uniformly.

Further, in this method, it is also preferred that during the stirring process, rotation speed control of the mixing screw is carried out by switching a rotation speed mode between at least two modes having different rotation speeds. In this case, it is preferred that the rotation speed mode of the mixing screw is switched at least 2 times per one minute. Further, it is also preferred that the rotation speeds of the mixing screw in the rotation speed modes have a difference of at least 5.0 rpm. These methods also make it possible to mix the components more uniformly.

In this method, preferably, the molding step is carried out by means of extrusion molding.

These and other objects, structures and advantages of the present invention will be apparent more clearly from the following description of the invention based on the examples.

DETAILED DESCRIPTION OF THE PREFERRED EMBODIMENTS

Figure 1:
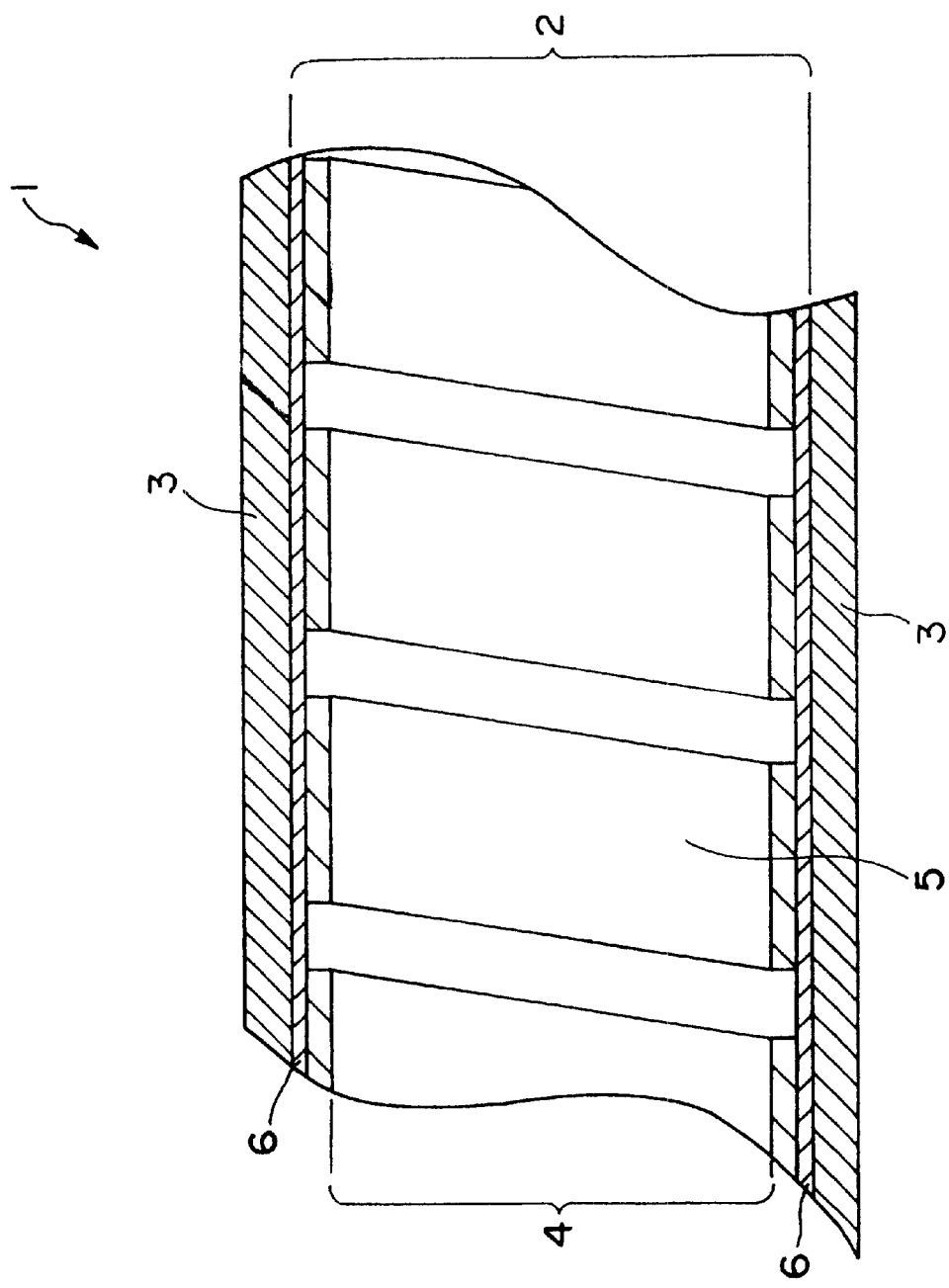
FIG. 1 is a partial cross-sectional view which shows a flexible tube for an endoscope.

Hereinafter, a flexible tube for an endoscope according to the present invention, a material used for producing an outer cover of the flexible tube, and a method of producing such a flexible tube will be described with reference to the appended drawings. (In the following description, the material used for producing the outer cover of the flexible tube will be referred to as "outer cover material.") In this connection, it is to be noted that the flexible tube is used in an insertion section of an endoscope which is designed to be inserted into a body cavity of a living body.

First, the outer cover of the flexible tube according to the present invention is made of a material which contains polyurethane elastomer and polyester elastomer, in which the compounding ratio of the polyurethane elastomer and the polyester elastomer in the material is 0.03–0.3 parts by weight of the polyester elastomer per 1 part by weight of the polyurethane elastomer.

By using the outer cover made of the material containing the polyurethane elastomer and the polyester elastomer which are mixed in the above-mentioned compounding ratio, it is possible to provide a flexible tube for an endscope having flexibility which is a characteristic of the polyurethane elastomer as well as chemical resistance and heat resitance which are characteristics of the polyester elastomer.

Hereinbelow, the present invention will be described in more details.

1. Components of Outer Cover Material

First, a description is made with regard to components which constitute the outer cover material for the outer cover of the flexible tube according to the present invention (hereinafter, simply referred to as "components").

(1-1) Polyurethane Elastomer

As for polyurethane elastomer to be used in this invention, for example, copolymers having hard segments and soft segments (such as random copolymers, block copolymers and the like) can be used.

Examples of the hard segments include polymers which contain diisocyanate and short chain glycol, polymers which contain short chain glycol as a main component thereof, and the like.

In this connection, examples of the diisocyanate include 4,4'-diphenylmethane diisocyanate (MDI), 2,4'-toluene diisocyanate (TDI), 2,6-toluene diisocyanate (TDI), 1,6-hexamethylene diisocyanate (HDI), 3,3'-dimethyldiphenyl-4,4'-diisocyanate (TODI), 1,5'-naphthalene diisocyanate (NDI), and the like. Among these substances, 4,4'-diphenylmethane diisocyanate (MDI) should preferably be used in this invention.

Further, examples of the short chain glycol include ethylene glycol (EO), 1,3-propylene glycol (PG), 1,3-butylene glycol, 1,4-butylene glycol, 1,6-hexyl glycol, 1,4-dimethylolbenzene, bisphenol A, bisphenol A/EO, and the like. Among these substances, 1,4-butylene glycol should preferably be used in this invention.

Examples of the soft segments include polymers which contain diisocyanate and long chain glycol, polymers which contain long chain glycol as a main component thereof, and the like.

In this connection, examples of the diisocyanate include substances which are the same as those mentioned with reference to the hard segments, and among those substances 4,4'-diphenylmethane diisocyanate (MDI) should preferably be used in this invention.

Further, examples of the long chain glycol include polytetra methylene ether glycol (PTMG), poly(oxypropylene) glycol, poly(ethylene adipate)glycol, poly(butylene-1,4-adipate)glycol, poly(ethylene-1,4-adipate)glycol, poly(hexanediol-1,6-carbonate) glycol, polycaprolactone glycol, poly(diethylene glycol adipate)glycol, (hexanediol-1,6-carbonate)glycol, and the like. Among these substances, polytetra methylene ether glycol (PTMG) should preferably be used in this invention.

These kinds of polyurethane elastomer have excellent flexibility. For this reason, when the polyurethane elastomer described above is used as one of the main components of the outer cover material, it is possible to obtain a flexible outer cover that is particularly suitable for a flexible tube for an endoscope. Further, since the polyurethane elastomer has a high compatibility with the polyester elastomer, it is possible to obtain an outer cover material which contains the polyurethane elastomer and the polyester elastomer in a uniformly mixed state.

(1-2) Polyester Elastomer

As for polyester elastomer to be used in this invention, for example, copolymers having hard segments and soft segments (such as random copolymers, block copolymers and the like) can be used.

In this regard, the polyester elastomer is classified into a polyester-polyether type polyester elastomer, a polyester—polyester type polyester elastomer, and a liquid crystal type polyester elastomer.

Examples of hard segments of the polyester-polyether type polyester elastomer include polybutylene terephthalate (PBT), polyethylene terephthalate (PET), and the like.

Examples of soft segments of the polyester-polyether type polyester elastomer include polytetra methylene ether glycol (PTMG), poly(1,2-propylene oxide)glycol, poly(ethylene oxide) glycol, and the like.

Examples of hard segments of the polyester—polyester type polyester elastomer include polybutylene terephthalate (PBT), and the like.

Examples of soft segments of the polyester—polyester type polyester elastomer include polycaprolactone, and the like.

Further, examples of hard segments of the liquid crystal type polyester elastomer include dihydroxy paraquarterphenyl (DHQ), and the like.

Example of soft segments of the liquid crystal type polyester elastomer include aromatic-based polyester (e.g., polyethylene terephthalate), and the like.

Among these substances described above, the polybutylene terephthalate should preferably be used for the hard segments of the polyester elastomer. Further, the polytetra methylene ether glycol should preferably be used for the soft segments of the polyester elastomer.

These kinds of polyester elastomer have excellent chemical resistance and heat resistance. In contrast with this, the polyurethane elastomer by itself has insufficient chemical resistance and heat resistance. Therefore, when the polyester elastomer and the polyurethane elastomer are mixed to obtain an outer cover material, it becomes possible to improve chemical resistance property and heat resistance property of an outer cover of a flexible tube for an endoscope. Further, since such polyester elastomer has a high compatibility with the polyurethane elastomer, it is possible to obtain an outer cover material which contains the polyurethane elastomer and the polyester elastomer in a uniformly mixed state.

In this invention, the weight average molecular weight of the polyester elastomer is not limited to any particular values, but should preferably lie within the range 10,000–50,000, and more preferably lie within the range 18,000–40,000. In this regard, in order to obtain an outer cover material in a uniformly mixed state, components for the outer cover material should be sufficiently melted or softened before mixing these components. Now, when a polyester elastomer whose weight average molecular weight lies within the preferred ranges described above is subjected to heating treatment, the polyester elastomer becomes a molten state having relatively low viscosity. Accordingly, in the case where this kind of polyester elastomer is mixed with polyurethane elastomer, it is possible to obtain an outer cover material having a high degree of uniformity.

(1-3) Other Components

In addition to the polyurethane elastomer and the polyester elastomer described above, any desired additives may be added to the components used for preparing the outer cover material, as needed.

Examples of the additives include plasticizers, other thermoplastic elastomers, rubbers, inorganic fillers, pigments, various stabilizers (such as antioxidants, light stabilizers, antistatic agents, antiblocking agents, lubricants, and the like), x-ray imaging agents, and the like.

2. Compounding Ratio of Polyurethane Elastomer and Polyester Elastomer

Preferably, the compounding ratio of the polyester elastomer and the polyurethane elastomer in the outer cover material is 0.03–0.3 parts by weight of the polyester elastomer per 1 part by weight of the polyurethane elastomer. In this case, it is more preferable that the compounding ratio is 0.04–0.2 parts by weight of the polyester elastomer per 1 part by weight of the polyurethane elastomer, and it is most preferable that the compounding ratio is 0.05–0.15 parts by weight of the polyester elastomer per 1 part by weight of the polyurethane elastomer.

In the case where the compounding ratio of the polyester elastomer with respect to the polyurethane elastomer is less than the lower limit of the range described above, the chemical resistance and heat resistance imparted by the polyester elastomer will be insufficient. On the other hand, in the case where the compounding ratio of the polyester elastomer with respect to the polyurethane elastomer is greater than the upper limit of the range described above, the flexibility imparted by the polyurethane elastomer will be lowered. Namely, if the compounding ratio of the polyester elastomer with respect to the polyurethane elastomer is greater than the upper limit of the range described above, the outer cover of the flexible tube tends to have a large resilience. This will lower the operability (flexibility) of the insertion section of the endoscope, thus making it difficult to carry out delicate movements of the insertion section, which may result in the case that the burden on patients will be increased.

On the other hand, in the case where the compounding ratio of the polyester elastomer and the polyurethane elastomer lies within the range described above, it becomes possible for the flexible tube (that is, the outer cover of the flexible tube) to have sufficient flexibility, chemical resistance and heat resistance. Namely, by constructing an insertion section of an endoscope using the flexible tube having such an outer cover, it becomes possible to produce an endoscope with an insertion section having sufficient flexibility, chemical resistance and heat resistance.

3. Structure of Flexible Tube for Endoscope and Method of Producing the Flexible Tube Next, the structure of the flexible tube for an endoscope and the method of producing the flexible tube will be described with reference to the appended drawings.

First, with reference to FIG. 1, the structure of the flexible tube used in an insertion section of an endoscope according to the present invention will be described. In this regard, FIG. 1 is a partial cross-sectional view which shows the flexible tube.

As shown in the drawing, the flexible tube 1 is used in an insertion section of an endoscope which is designed to be inserted into a body cavity of a living body. As shown in FIG. 1, this flexible tube 1 is composed of a flexible elongated structural body 2 and an outer cover 3 which covers the outer periphery of the structural body 2. Further, inside the flexible tube 1, there is formed a space 4 through which internal elements (such as optical fibers, cables, tubular elements, and the like which are not shown in the drawings) can be passed.

The structural body 2 of the flexible tube 1 acts as a reinforcing member for reinforcing the flexible tube 1, and also acts as a protecting member for protecting the internal elements described above. This structural body 2 is constructed from a coil 5 and a reticular tube (layer) 6 which covers the outer periphery of the coil 5, so that the structural body 2 is formed into an elongated tubular shape. By constructing the structural body 2 using the coil 5 and the reticular tube 6, it becomes possible to give the flexible tube 1 torque transmission ability, tracking ability to a body cavity (i.e., bendability) and sufficient mechanical strength.

The coil 5 is formed from a flat metal band. Specifically, this coil 5 is formed by winding the metal band into a spiral form so as to have a uniform diameter and to provide a predetermined space between the adjacent windings. Preferred examples of materials which may be used for the metal band include stainless steel, copper alloys, and the like.

The reticular tube 6 can be formed from fine metal wires woven together or from fine metal wires and nonmetal fibers woven together. Preferred examples of materials which may be used for the fine metal wires include stainless steel, copper alloys and the like. Further, preferred examples of materials which may be used for the nonmetal fibers include synthetic resin such as polyester, polyamide, polyvinyl chloride and the like.

As shown in FIG. 1, the outer cover 3 (which is made of the material described above) of the flexible tube 1 covers the outer periphery of the structural body 2. By providing such an outer cover 3, it becomes possible to improve the ease of the inserting operation (that is, its flexibility) and to reduce the burden on patients. Further, it also becomes possible to prevent body fluids and the like from entering the inside of the endoscope (in particular, the insertion section of the endoscope).

In this invention, the thickness of the outer cover 3 is not limited to a specific value if the outer cover can exhibit its function that protects the structural body 2 and does not deteriorate the bendability of the flexible tube 1. However, normally, it is preferable that the outer cover 3 is formed so as to have a thickness in the range of approximately 0.05–0.85 mm, and more preferably in the range of approximately 0.10–0.70 mm.

In the foregoing, a description has been made with regard to the case where the flexible tube of the present invention is used in an insertion section of an endoscope. However, it is to be noted that the flexible tube having the outer cover described above can also be used in other parts in an endoscope system such as an outer tube for a light guiding cable connected to a light source apparatus of the endoscope system.

Figure 2:
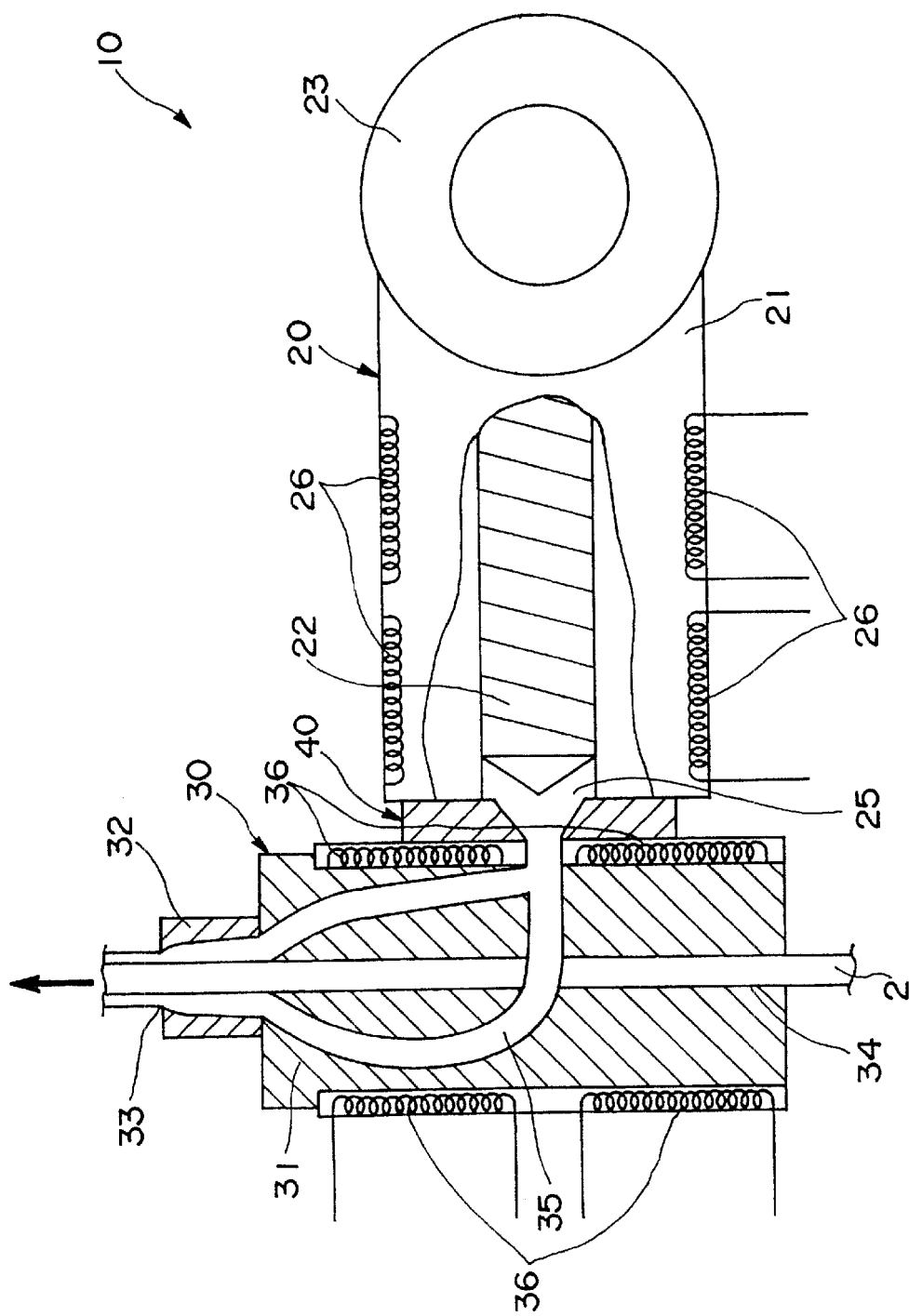
FIG. 2 is a partial cross-sectional view which shows an extruder used for producing the flexible tube according to the present invention.

Next, the method of producing the flexible tube having the outer tube will be described with reference to FIGS. 2 and 3. In this regard, FIG. 2 is a partial cross-sectional view which shows an extruder used for producing the flexible tube according to the present invention. Further, FIG. 3 is a side view of the extruder shown in FIG. 2.

Figure 3:
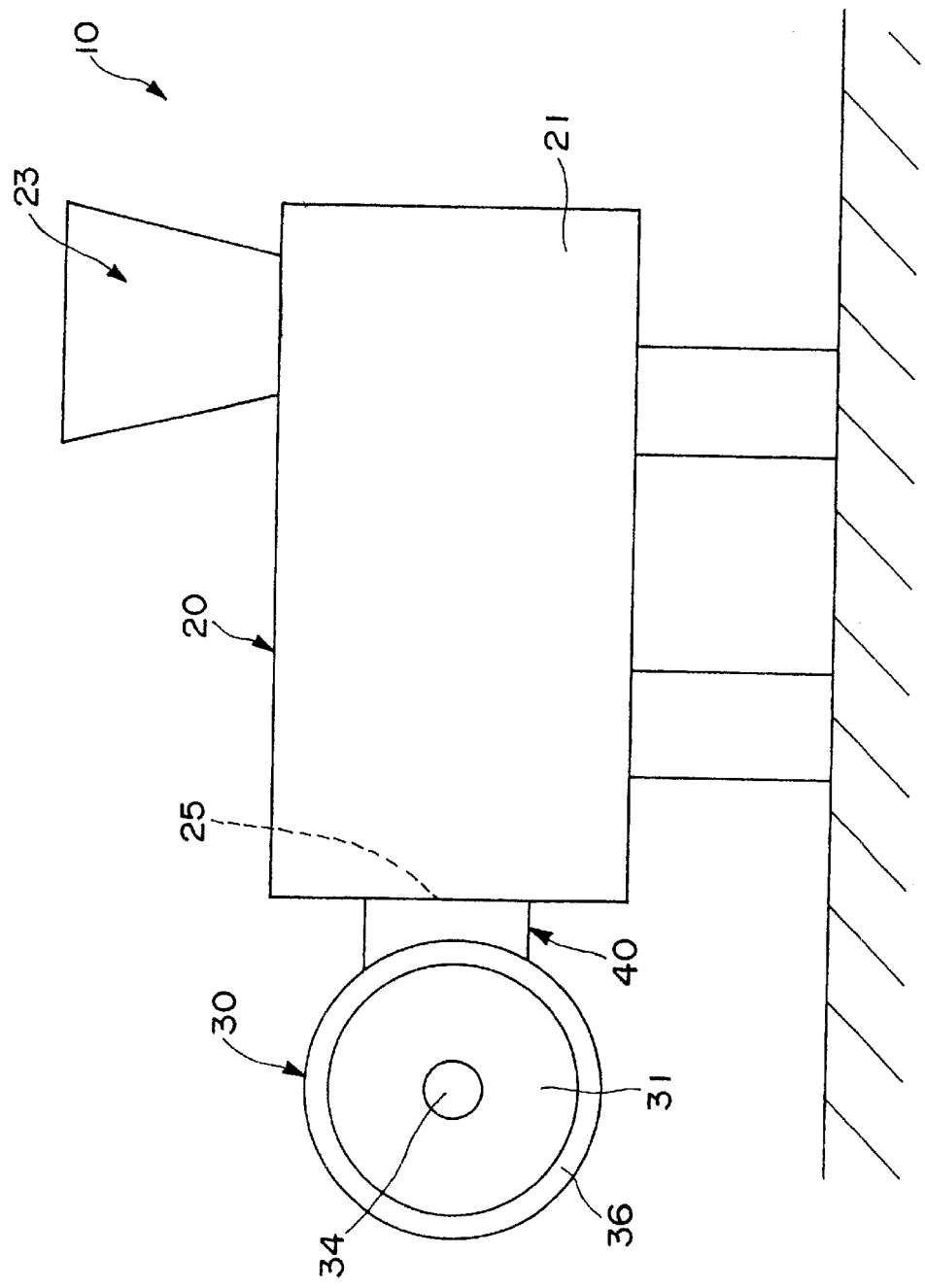
FIG. 3 is a side view of the extruder shown in FIG. 2.

The extruder 10 shown in FIGS. 2 and 3 is used for producing the outer cover 3 of the flexible tube 1. Namely, the extruder 10 is used for providing the outer cover 3 made of the outer cover material onto the outer periphery of the structural body 2 so that the structural body 2 is covered with the outer cover 3.

In this invention, the outer cover 3 of the flexible tube 1 is formed using the extruder 10 in accordance with the following steps (i)–(iii).

(i) The outer cover material which is a mixture containing the polyurethane elastomer and the polyester elastomer and the like is prepared. In this connection, the compounding ratio of the polyurethane elastomer and the polyester elastomer in the material is 0.03 to 0.3 parts by weight of the polyester elastomer per 1 part by weight of the polyurethane elastomer. It is preferred that in this step the material is stirred (mixed) so that the polyurethane elastomer and the polyester elastomer uniformly mixed to each other.

(ii) The prepared material is heated to such an extent that the material is melted or softened.

(iii) The material is then extruded onto the structure body 2 so as to form an elongated tubular body to obtain the flexible tube having the outer cover.

According to the method described above, it is possible to produce the flexible tube having the outer cover in which the components described above are contained in a uniformly mixed state.

Hereinafter, the method of producing such a flexible tube will be described in more detail.

As shown in FIGS. 2 and 3, the extruder 10 has a mixing section 20 and a head section 30. Further, as shown in FIG. 3, the head section 30 is fixed to the mixing section 20 by means of a support body 40.

In the mixing section 20, the individual components are melted or softened, and then mixed together to obtain the outer cover material. Further, in the head section 30, the outer cover material obtained by mixing the components is extruded so that the outer periphery of the structural body 2 is covered with the outer cover material in the form of an elongated tubular body.

The mixing section 20 of the extruder 10 has a cylinder 21 equipped with an mixing screw 22 for mixing the components, a hopper 23 connected to the cylinder 21, and an opening 25 through which the outer cover material is fed to the head section 30 of the extruder 10.

Specifically, when producing the flexible tube, first each of the components described above is poured into the cylinder 21 through the hopper 23. Next, in the cylinder 21, each of the components is melted or softened under heated condition, and then mixing process is carried out by the mixing screw 22 rotating at a predetermined rotation speed.

As shown in FIG. 2, a heater 26 is provided on the outer periphery of the cylinder 21 to heat the cylinder 21. The heater 26 is also used to maintain the temperature inside the cylinder 21 at a predetermined temperature accurately. Consequently, each component poured into the cylinder 21 is sufficiently melted or softened.

The temperature (mixing temperature) inside the cylinder 21 is not limited to any particular values, but should preferably lie within the range of approximately 140–230° C., and more preferably lie within the range of approximately 150–220° C. If the temperature inside the cylinder 21 is below the lower limit of such range, there will be cases where the components will not be sufficiently melted or softened. On the other hand, if the temperature inside the cylinder 21 exceeds the upper limit of such range, there will be cases where the components will decompose or deteriorate.

It is preferred that the extruder used in this invention is provided with a single mixing screw. However, there is no particular limitation on the number of the mixing screw to be provided in the extruder if the components can be uniformly mixed. For example, the extruder may be provided with two or more mixing screws.

The rotation speed of the mixing screw 22 is not limited to any particular values, but should preferably lie within the range of 2.0 to 30 rpm (at average rotation speed), and more preferably within the range of 3.5 to 20 rpm. If the rotation speed of the mixing screw 22 is slower than the lower limit of the range, there will be cases where it is not possible to uniformly mix the components. On the other hand, if the rotation speed of the mixing screw 22 is faster than the upper limit of the range, the components will decompose and deteriorate during the mixing process in the case where the temperature inside the cylinder 21 is too high.

In this invention, it is preferred that the rotation speed control of the mixing screw is carried out by switching the rotation speed mode between at lease two modes having different rotation speeds (i.e., high and low rotation-speed modes), and more preferably between any of 2 to 10 modes.

In this connection, it is well known that a good mixability which provides a uniform mixing is achieved when the mixing screw 22 is rotated at a high rotation speed. However, it is to be noted that, as described above, in the case where the components are being stirred (mixed) at a high rotation speed for a long period of time under high temperature conditions, there is a case that the components will decompose or deteriorate. In view of the fact described above, in this embodiment, the rotation speed control of the mixing screw 22 is carried out by switching the rotation speed mode of the mixing screw 22 between the high and low rotation speed modes. By controlling the rotation speed of the mixing screw in this way, it becomes possible to obtain the outer cover material in which the components are uniformly mixed. Further, this rotation speed control also makes it possible to prevent the components from decomposing and deteriorating during the mixing process, which is one of the merits of the low rotation speed mode. Namely, use of the rotation speed control described able makes it possible to provide a high quality outer cover for a flexible tube which has a good uniformity of the components and which is hard to decompose nor deteriorate during the mixing process.

In order to further improve the uniformity of the outer cover material, the rotation-speed mode of the mixing screw 22 should preferably be switched at least 2 times per one minute, and more preferably 2 to 5 times per one minute.

Further, in order to further improve the uniformity of the outer cover material, the rotation speeds of the mixing screw in the rotation-speed modes should preferably have a difference of at least 5.0 rpm, and more preferably a difference of 5.0 to 16.5 rpm.

The outer cover material prepared in the mixing section 20 in this way is fed to the opening 25 with the rotation of the mixing screw 22. Then, the outer cover material in a molten or softened state is supplied from the mixing section 20 to the head section 30 through the opening 25.

The head section 30 of the extruder 10 has a cross head 31, a die 32 and a nozzle 33. Further, the head section 30 has a first passageway 34 through which the structural body 2 is to be passed, and a second passageway 35 through which the outer cover material is to be fed from the opening 25 to the nozzle 33. The first and second passageways 34, 35 are formed inside the cross head 31 of the head section 30.

When producing the flexible tube 1, the structural body 2 is passed through the first passageway 34, and then the structural body 2 is conveyed (by conveying means not shown in the drawings) into the die 32 in the direction shown by the arrow in FIG. 2, and then passed therethrough.

The second passageway 35 is formed inside the cross head 31 with a predetermined bend roughly perpendicular to the central axis of the mixing screw 22. Further, the second passageway 35 is bifurcated into two branches in the cross head 31 near the opening 25. These two branches are then joined together near the die 32.

Further, as shown in FIG. 2, a heater 36 is provided on the outer peripheral portion of the cross head 31. Consequently, when the outer cover material passes through the second passageway 35, the outer cover material is heated to a predetermined temperature by the heater 36, and thus heated outer cover material in a molten or softened state is fed to the die 32 through the second passageway 35. Accordingly, when the outer cover material is extruded from the nozzle 33, the outer cover material in a molten or softened state comes into contact with the outer periphery of the structural body 2 at the die 32. In this way, the outer cover material is being extruded in such a manner that the structural body 2 is continuously covered with the outer cover (that is, in such a manner that an elongated tubular body made from the outer cover material is provided onto the outer periphery of the structural body 2).

The temperature of the head section 30, namely, the temperature of the outer cover material before molding is not limited to any particular values, but should preferably lie within the range 140 to 230° C., and more preferably lie within the range of 155 to 215° C. If the temperature of the head section 30 is below the lower limit of the former range, there are cases where the outer cover material solidifies. On the other hand, if the temperature of the head section 30 exceeds the upper limit of the range, there are cases where the outer cover material will decompose or deteriorate.

Further, the viscosity of the outer cover material before molding is not limited to any particular values, but should preferably lie within the range of $1.0 \times 10^2$ to $1.0 \times 10^7$ ps, and more preferably lie within the range of $2.0 \times 10^2$ to $8.0 \times 10^5$ ps. In the case where the viscosity of the outer cover material before molding lies within such range, the outer cover of the flexible tube will have excellent weather resistance.

In this connection, it is to be noted that the nozzle (extrusion opening) 33 is formed to have a roughly circular shape. Further, it is also to be noted that the center of the nozzle 33 substantially coincides with the center of a cross section of the structural body 2. In this way, the outer cover 3 which covers the outer periphery of the structural body 2 is formed so as to have a substantially uniform thickness within the range described above.

In the foregoing, the flexible tube for an endoscope according to the present invention and the method of producing the flexible tube have been described with reference to the embodiment shown in the drawings. However, it should be noted that the method of producing a flexible tube for an endoscope of the present invention is not limited thereto. For example, a flexible tube for an endoscope may be produced in the following manner. Namely, first the outer cover material is formed into an elongated tubular body to obtain the outer cover for covering the outer periphery of the structural body 2, and then the structural body 2 is inserted into thus obtained outer cover having an elongated tubular shape. Next, bonding treatment such as heating is carried out to the outer cover in which the structural body has been inserted, to produce a flexible tube for an endoscope.

Further, the method of producing the flexible tube described above can be applied to, for example, a method of producing a flexible tube for guiding cables connected to a light source device of an endoscope system.

EXAMPLES

Next, specific examples of the present invention will be described below.

Example 1

In this Example, the following polyurethane elastomer and polyester elastomer were used to obtain an outer cover material.

Polyurethane Elastomer: A block copolymer having hard segments of 1,4-butylene glycol and soft segments of polytetra methylene ether glycol.

Polyester Elastomer: Block copolymer having hard segments of polybutylene terephthalate and soft segments of polytetra methylene ether glycol. (In this case, the weight average molecular weight of the polyester elastomer was 10,000.)

First, a structural body was made from a stainless steel coil and a reticular tube formed by weaving together stainless steel metal wires and nonmetal polyester fibers.

Next, using an extruder having a mixing screw, the polyurethane elastomer and the polyester elastomer in the compounding ratio shown in Table 1 were mixed with the mixing screw at a temperature of 180° C. During the mixing process, the rotation speed of the mixing screw was alternately switched between a high rotation speed (16 rpm) and a low rotation speed (5 rpm) at a switching rate of 5 times per one minute. In this way, an outer cover material used for making an outer cover of a flexible tube for an endoscope was obtained.

Further, in this Example, the outer cover material was extruded from the nozzle of the head section of the extruder onto the outer periphery of the structural body 2 to form an outer cover 3 in the form of an elongated tubular body having a thickness of 0.5 mm. During this extrusion process, the head section of the extruder was being held at a temperature of 180° C. In this way, a flexible tube for an endoscope having an inner diameter of 7 mm, an outer diameter of 9 mm and a length of 1.5 m was produced.

In accordance with the processes described above, a plurality of flexible tubes were produced. In this connection, each of the flexible tubes had any one of the outer cover materials shown by the sample numbers 1–11 in Table 1. Specifically, as shown in Table 1, the outer cover materials of the sample numbers 1–11 had different compounding ratios. The sample numbers 2–9 were produced using the outer covers made of the outer cover material according to the present invention, and the sample numbers 1, 10 and 11 were produced using outer covers made of conventional material. These outer covers of the sample numbers 1, 10 and 11 were prepared for the purpose of comparison with the outer covers made of the outer cover material of the present invention.

Evaluation of Flexible Tubes

For each of the flexible tubes prepared in this way, a flexibility test, a chemical resistance test, a heat resistance test and a weather resistance test were carried out, respectively, as described below.

1. Flexibility Test

In the flexibility test, ten flexible tubes were prepared for each type of the flexible tubes of the sample numbers 1–11, and these ten flexible tubes were bundled together in each type of the samples. Using these bundled ten flexible tubes, an experiment was made to know as to whether the bundled flexible tubes could be bent or not for each of the samples. The results of the experiments were evaluated in accordance with the four rankings A–D given below.

A: Excellent Flexibility
B: Good Flexibility
C: Poor Flexibility
D: Almost No Flexibility (Stiff State)

2. Chemical Resistance Test

The chemical resistance test was carried out on each of sheet-shaped test samples made from the outer cover materials used for making the outer covers of the flexible tubes of the sample numbers 1–11. In this regard, each of the sheet-shaped test samples had a thickness of 0.5 mm, a length of 30 mm and a width of 10 mm.

In the chemical resistance test, each test sample was examined to determine whether or not it swelled or dissolved in a solution of dimethylformamide (DMF).

Namely, each test sample was submerged in 20 mL of the dimethylformamide (DMF) solution kept at 25° C. for one week. Then, an examination was carried out to determine the change in volume of each test sample by comparing the volume of each test sample after one week of submersion in the DMF solution with the volume of each test sample before submersion in the DMF solution. The results of the examinations were evaluated in accordance with the four rankings A–D given below.

A: Insoluble in DMF
B: Swelling Below 5% by Volume
C: Swelling Below 10% by Volume
D: Swelling Above 10% by Volume, or Soluble in DMF 3. Heat Resistance Test The heat resistance test was carried out on each of sheet-shaped test samples which were made of the outer cover materials used for making the outer covers of the flexible tubes of the sample numbers 1–11. In this regard, each of the sheet-shaped test samples had a thickness of 0.5 mm, a length of 30 mm and a width of 10 mm.

In the heat resistance test, each test sample was repeatedly subjected to heating and rapid cooling (quenching), and then an examination was carried out to determine whether or not the flexibility was degraded.

In more detail, in one heating/cooling operation, each test sample was subjected to autoclave sterilization for 15 minutes at a temperature of 135° C. and a pressure of 2.2 atmospheres, and then quenched in ice water. This heating/cooling operation was carried out ten times for each test sample.

After such heating/cooling operation was carried out ten times for each test sample, the degree of degradation, namely, the loss in flexibility was examined by comparing the flexibility of each test sample after the ten times heating/cooling operations with the flexibility of each test sample before the ten times heating/cooling operations. The results of the examinations were evaluated in accordance with the four rankings A–D given below.

A: Almost No Change in Flexibility
B: Slight Change in Flexibility
C: Lowering of Flexibility
D: Stiff State (Significant Degradation)

4. Weather Resistance Test

The weather resistance test was carried out on each of sheet-shaped test samples made from the outer cover materials used for making the outer covers of the flexible tubes of the sample numbers 1–11. In this regard, each of the sheet-shaped test samples had a thickness of 0.5 mm, a length of 30 mm and a width of 10 mm.

In the weather resistance test, each test sample was irradiated with ultraviolet light, and then an examination was carried out to determine whether or not there was a change in its resilience.

Namely, an ultraviolet lamp was used to irradiate each test sample for one hour with ultraviolet light having a wavelength of 250–380 nm at an intensity of 20 m W/cm$^2$.

Then, after each test sample was irradiated with ultraviolet light for one hour, an examination was made to determine the change in the resilience of each test sample by comparing the resilience of each test sample after ultraviolet irradiation with the resilience of each test sample before ultraviolet irradiation. The results of the examinations were evaluated in accordance with the four rankings A–D given below.

A: Almost No Change in Resilience
B: Slight Change in Resilience
C: Lowering of Resilience (Slight Stiffening)
D: Stiff State (Significant Degradation)

Each of the test results in Example 1 described above are shown in the attached Table 1.

Example 2

Outer covers and flexible tubes having the outer covers were produced in the same manner as in Example 1 except that polyester elastomer having a weight average molecular weight of 20,000 was used as one of the components for the outer cover material.

Each of such flexible tubes were evaluated through the Tests 1–4 described above, and the evaluation results for each flexible tube in Example 2 are shown in the attached Table 2.

Example 3

Flexible tubes for an endoscope having the same dimensions as the flexible tubes in Example 1 were produced in the same manner as in Example 1 except that a polyester elastomer having a weight average molecular weight of 35,000 was used.

Each of such flexible tubes were evaluated through the Tests 1–4 described above, and the evaluation results for each flexible tube in Example 3 are shown in the attached Table 3.

Example 4

Flexible tubes for an endoscope having the same dimensions as the flexible tubes in Example 1 were produced in the same manner as in Example 1 except that a polyester elastomer having a weight average molecular weight of 50,000 was used.

Each of such flexible tubes were evaluated through the Tests 1–4 described above, and the evaluation results of such tests for each flexible tube in Example 4 are shown in the attached Table 4.

The test results in Tables 1–4 show that the flexible tubes of the sample Numbers 2–9, 13–20, 24–31, and 35–42 have good flexibility, chemical resistance, heat resistance and good weather resistance. This means that the flexible tubes having the outer cover made from the outer cover material of this invention have good flexibility, chemical resistance, heat resistance and good weather resistance.

Further, the test results also show that the flexible tubes of the sample numbers 4–6, 15–17, 26–28, and 37–39 have particularly good flexibility, chemical resistance, heat resistance and weather resistance. This means that the flexible tube having the outer cover made from the outer cover material of this invention (which contains 0.05–0.15 parts by weight of the polyester elastomer with respect to 1 part by weight of the polyurethane elastomer) have particularly good flexibility, chemical resistance, heat resistance and weather resistance.

Furthermore, the test results also show that the flexible tubes (i.e., flexible tubes in each of Examples 2 and 3) having the outer covers made of the outer cover material of this invention (which contains a polyester elastomer having a weight average molecular weight of 18,000–40,000) have particular good flexibility, chemical resistance, heat resistance and weather resistance.

In contrast, the test results show that the flexible tubes having the outer covers of the sample numbers 1, 12, 23 and 34 (in which the compounding ratio of the polyester elastomer is small) have poor chemical resistance, heat resistance and weather resistance. This means that the flexible tubes having the outer covers made from the conventional outer cover material have poor chemical resistance, heat resistance and weather resistance.

Further, the test results also show that the flexible tubes having the outer covers of the sample numbers 10, 11, 21, 22, 32, 33, 43 and 44 (in which the compounding ratio of the polyester elastomer is large) have good chemical resistance, heat resistance and weather resistance, but poor flexibility. This means that the flexible tubes having the outer covers made of the outer cover material having a high polyester elastomer content have good chemical resistance, heat resistance and weather resistance, but poor flexibility.

Example 5

In this Example, the following polyurethane elastomer and polyester elastomer were used to obtain outer cover material.

Polyurethane Elastomer: Block copolymer having hard segments of 1,4-butylene glycol and soft segments of polytetra methylene ether glycol.

Polyester Elastomer: Block copolymer having hard segments of polybutylene terephthalate and soft segments of polytetra methylene ether glycol. (In this case, the weight average molecular weight of the polyester elastomer was 30,000.)

First, a structural body was made from a stainless steel coil and a reticular tube formed by weaving together stainless steel metal wires and nonmetal polyester fibers.

Next, using an extruder with a mixing screw, the polyurethane elastomer and the polyester elastomer at a compounding ratio of 0.1 parts by weight of the polyester elastomer with respect to 1 part by weight of the polyurethane elastomer were mixed with the mixing screw at a temperature of 180° C. During this mixing process, the rotation speed of the mixing screw was alternately switched between a high rotation speed (20 rpm) and a low rotation speed (5 rpm) at a switching rate of 4 times per one minute. In this way, outer cover material used for making an outer cover of a flexible tube for an endoscope was obtained.

Next, by adjusting the temperature of the head section of the extruder, the temperature and the viscosity of the outer cover material before molding were set at the values shown in Table 5. Then, the outer cover material was extruded from the nozzle of the head section of the extruder onto the outer periphery of the structural body 2 to form an outer cover 3 in the form of an elongated tubular body having a thickness of 0.5 mm. During this extrusion process, the head section of the extruder was being held at a temperature of 180° C. In this way, a flexible tube for an endoscope having an inner diameter of 7 mm, an outer diameter of 9 mm and a length of 1.5 m was produced. (In this regard, it is to be noted that measurements of viscosity in a molten state were carried out using a process viscometer of the capillary type.)

Evaluation for Flexible Tubes in Example 5

The flexible tubes obtained in this way were subjected to a weather resistance test.

Namely, the weather resistance test was carried out in the same manner as described above, and the results of such weather resistance test for Example 5 are shown in the attached Table 5.

The test results in Table 5 show that the flexible tubes having the outer covers of the sample numbers 45–51 have good weather resistance property. Further, the results also show that the flexible tubes having the outer covers of the sample numbers 46–49 have even better weather resistance property.

Namely, the test results in Table 5 show that when the temperature and viscosity of the outer cover material before molding are set at appropriate values, flexible tubes having the outer covers made of the outer cover material of this invention will have good weather resistance. In particular, when the temperature of the outer cover material before molding is in the range 155–215° C. and the viscosity thereof is in the range $2.0\times10^2$–$8.0\times10^5$ ps, the outer cover made of the outer cover material will have even better weather resistance.

As described above, according to the present invention, it is possible to produce a flexible tube for an endoscope having flexibility which is a characteristic of polyurethane elastomer and chemical resistance and heat resistance which are characteristics of polyester elastomer, since the outer cover of the flexible tube is made of outer cover material that contains the polyurethane elastomer and the polyester elastomer. Further, since the flexible tube of the present invention has the outer cover made of the above material, the flexible tube exhibits excellent weather resistance.

Further, by adjusting the weight average molecular weight of the polyester elastomer and the viscosity of the outer cover material in a molten state, it is possible to further improve the results described above.

Furthermore, the present invention makes it possible to obtain a flexible tube for an endoscope in which each portion of the outer cover of the flexible tube has uniform flexibility, chemical resistance, heat resistance and weather resistance.

Finally, it is to be understood that many changes and additions may be made to the embodiments described above without departing from the scope and spirit of the invention as defined in the appended Claims.

Further, it is also to be understood that the present disclosure relates to subject matter contained in Japanese Patent Application No. 11-353541 (filed on Dec. 13, 1999) which is expressly incorporated herein by reference in its entirety.

TABLE 1

<EXAMPLE 1>

|  | Sample No. | Compounding Ratio* [Parts by Weight] | Flexibility Test | Chemical Resistance Test | Heat Resistance Test | Weather Resistance Test |
|---|---|---|---|---|---|---|
| Sample of Compar. Ex. | 1 | 0.02 | A | D | D | D |
| Samples | 2 | 0.03 | A | B | B | B |
| of | 3 | 0.04 | A | B | B | B |
| This Invention | 4 | 0.05 | A | A | A | A |
|  | 5 | 0.10 | A | A | A | A |
|  | 6 | 0.15 | A | A | A | A |
|  | 7 | 0.20 | B | A | A | A |
|  | 8 | 0.25 | B | A | A | A |
|  | 9 | 0.30 | B | A | A | A |
| Samples of Compar. Ex. | 10 | 0.35 | D | A | A | A |
|  | 11 | 0.40 | D | A | A | A |

Compounding Ratio*: This shows the compounding ratio of polyester elastomer with respect to 1 part by weight of polyurethane elastomer, in which the polyester elastomer has a weight average molecular weight of 10,000.

TABLE 2

<EXAMPLE 2>

|  | Sample No. | Compounding Ratio* [Parts by Weight] | Flexibility Test | Chemical Resistance Test | Heat Resistance Test | Weather Resistance Test |
|---|---|---|---|---|---|---|
| Sample of Compar. Ex. | 12 | 0.02 | A | D | C–D | D |
| Samples | 13 | 0.03 | A | B | B | B |
| of | 14 | 0.04 | A | B | B | B |
| This Invention | 15 | 0.05 | A | A | A | A |
|  | 16 | 0.10 | A | A | A | A |
|  | 17 | 0.15 | A | A | A | A |
|  | 18 | 0.20 | A | A | A | A |
|  | 19 | 0.25 | B | A | A | A |
|  | 20 | 0.30 | B | A | A | A |
| Samples of Compar. Ex. | 21 | 0.35 | C | A | A | A |
|  | 22 | 0.40 | D | A | A | A |

Compounding Ratio*: This shows the compounding ratio of polyester elastomer with respect to 1 part by weight of polyurethane elastomer, in which the polyester elastomer has a weight average molecular weight of 20,000.

TABLE 3

<EXAMPLE 3>

|  | Sample No. | Compounding Ratio* [Parts by Weight] | Flexibility Test | Chemical Resistance Test | Heat Resistance Test | Weather Resistance Test |
|---|---|---|---|---|---|---|
| Sample of Compar. Ex. | 23 | 0.02 | A | D | D | D |
| Samples | 24 | 0.03 | A | B | B | B |
| of | 25 | 0.04 | A | A | B | B |
| This Invention | 26 | 0.05 | A | A | A | A |
|  | 27 | 0.10 | A | A | A | A |
|  | 28 | 0.15 | A | A | A | A |
|  | 29 | 0.20 | A | A | A | A |
|  | 30 | 0.25 | B | A | A | A |
|  | 31 | 0.30 | B | A | A | A |
| Samples of Compar. Ex. | 32 | 0.35 | C–D | A | A | A |
|  | 33 | 0.40 | D | A | A | A |

Compounding Ratio*: This shows the compounding ratio of polyester elastomer with respect to 1 part by weight of polyurethane elastomer, in which the polyester elastomer has a weight average molecular weight of 35,000.

TABLE 4

<EXAMPLE 4>

|  | Sample No. | Compounding Ratio* [Parts by Weight] | Flexibility Test | Chemical Resistance Test | Heat Resistance Test | Weather Resistance Test |
|---|---|---|---|---|---|---|
| Sample of Compar. Ex. | 34 | 0.02 | A | D | D | D |
| Samples | 35 | 0.03 | A | B | B | B |
| of | 36 | 0.04 | A | A | A | B |
| This Invention | 37 | 0.05 | A | A | A | A |
|  | 38 | 0.10 | A | A | A | A |
|  | 39 | 0.15 | A | A | A | A |
|  | 40 | 0.20 | B | A | A | A |
|  | 41 | 0.25 | B | A | A | A |
|  | 42 | 0.30 | B | A | A | A |
| Samples of Compar. Ex. | 43 | 0.35 | D | A | A | A |
|  | 44 | 0.40 | D | A | A | A |

Compounding Ratio*: This shows the compounding ratio of polyester elastomer with respect to 1 part by weight of polyurethane elastomer, in which the polyester elastomer has a weight average molecular weight of 50,000.

TABLE 5

<EXAMPLE 5>

|  | Sample No. | Temperature of Material Before Molding [° C.] | Viscosity of Material Before Molding [ps] | Weather Resistance Test |
|---|---|---|---|---|
| Samples | 45 | 230 | $1.0 \times 10^2$ | B |
| of | 46 | 210 | $2.0 \times 10^2$ | A |
| This Invention | 47 | 200 | $1.0 \times 10^3$ | A |
|  | 48 | 190 | $1.0 \times 10^4$ | A |
|  | 49 | 160 | $5.0 \times 10^5$ | A |
|  | 50 | 150 | $1.0 \times 10^6$ | B |
|  | 51 | 140 | $1.0 \times 10^7$ | B |

What is claimed is:

1. A flexible tube for an endoscope comprising:
a flexible elongated structural body; and
an outer cover provided over the elongated structural body, the outer cover comprising polyurethane elastomer and polyester elastomer in a compounding ratio of 1 part by weight of the polyurethane per 0.03–0.2 parts by weight of the polyester.

2. The flexible tube of claim 1, comprising a compounding ratio of 1 part by weight of the polyurethane per 0.03–0.15 parts by weight of the polyester.

3. The flexible tube of claim 1, wherein the weight average molecular weight of the polyester elastomer lies within the range of 10,000–50,000.

4. The flexible tube of claim 1, wherein the polyurethane elastomer and the polyester elastomer are uniformly mixed.

5. A material used for producing an outer cover of a flexible tube for an endoscope, the material comprising polyurethane elastomer and polyester elastomer in a compounding ratio of 1 part by weight of the polyurethane per 0.03–0.2 parts by weight of the polyester.

6. The material of claim 5, comprising a compounding ratio of 1 part by weight of the polyurethane per 0.03–0.15 parts by weight of the polyester.

7. The material of claim 5, wherein the weight average molecular weight of the polyester elastomer lies within the range of 10,000–50,000.

8. The material of claim 5 wherein the polyurethane elastomer and the polyester elastomer are uniformly mixed.

9. A method of producing a flexible tube for an endoscope comprising:
preparing a material comprising polyurethane elastomer and polyester elastomer in a ratio of 1 part by weight of the polyurethane elastomer to 0.03–0.2 parts by weight of the polyester elastomer;
heating the material to such an extent that the material is melted or softened; and
molding the material onto a flexible elongated structural body to form an outer cover of the flexible tube in an elongated tubular form.

10. The method of claim 9, wherein the material prepared comprises polyurethane elastomer and polyester elastomer in a ratio of 1 part by weight of the polyurethane elastomer to 0.03–0.15 parts by weight of the polyester elastomer.

11. The method of claim 9, wherein the molding comprises extrusion molding.

12. The method of claim 9, wherein before the molding the temperature of the material is held at 140–230° C.

13. The method of claim 9, wherein before the molding, the viscosity of the material lies within the range of $1.0 \times 10^2$–$1.0 \times 10^7$ ps.

14. The method of claim 9, wherein the weight average molecular weight of the polyester elastomer lies within the range of 10,000–50,000.

15. The method of claim 9, wherein the preparing comprises stirring the material so that the polyurethane elastomer and the polyester elastomer are uniformly mixed.

16. The method of claim 15, wherein the preparing comprises pouring the material into a cylinder provided with a mixing screw, and stirring the material with the mixing screw under heated condition.

17. The method of claim 16, wherein the stirring comprises rotating the cylinder at a rotation speed of 2 to 30 rpm.

18. The method of claim 16, wherein the stirring comprises rotation speed control of the mixing screw comprising switching a rotation speed mode between at least two modes having different rotation speeds.

19. The method of claim 18, wherein the rotation speed mode of the mixing screw is switched at least two times per minute.

20. The method of claim 18, wherein the at least two modes having different rotation speeds have a difference of at least 5 rpm.

* * * * *